(12) United States Patent
Letard et al.

(10) Patent No.: US 8,709,599 B2
(45) Date of Patent: Apr. 29, 2014

(54) SPIN TRANSITION MATERIAL

(75) Inventors: Jean-François Letard, Canejan (FR); Nathalie Daro, Pessac (FR); Sandie Auffret, Bures-sur-Yvette (FR)

(73) Assignee: Centre National de la Recherche Scientifique, Paris (FR)

( * ) Notice: Subject to any disclaimer, the term of this patent is extended or adjusted under 35 U.S.C. 154(b) by 980 days.

(21) Appl. No.: 12/664,008

(22) PCT Filed: Jun. 11, 2008

(86) PCT No.: PCT/FR2008/000792
§ 371 (c)(1), (2), (4) Date: Dec. 10, 2009

(87) PCT Pub. No.: WO2009/007534
PCT Pub. Date: Jan. 15, 2009

(65) Prior Publication Data
US 2010/0178511 A1 Jul. 15, 2010

(30) Foreign Application Priority Data
Jun. 12, 2007 (FR) ..................................... 07 04174

(51) Int. Cl.
| | |
|---|---|
| C07F 15/00 | (2006.01) |
| C07F 15/02 | (2006.01) |
| C07F 15/04 | (2006.01) |
| C07F 15/06 | (2006.01) |
| C09C 1/22 | (2006.01) |
| G11B 7/249 | (2013.01) |
| C09B 45/00 | (2006.01) |
| G11B 7/246 | (2013.01) |

(52) U.S. Cl.
USPC ............... 428/402; 428/404; 540/3; 548/101; 548/107; 548/109

(58) Field of Classification Search
None
See application file for complete search history.

(56) References Cited

U.S. PATENT DOCUMENTS 5,582,900 A * 12/1996 Khan et al. ................. 428/195.1
2008/0311401 A1 * 12/2008 Letard et al. ................. 428/404

FOREIGN PATENT DOCUMENTS

WO    WO 2007/065996 A1 *  6/2007  .............. C07F 15/02

OTHER PUBLICATIONS van Koningsbruggen, P.J., Garcia, V., Codjovi, E., Lapouyade, R., Kahn., Fournes, L., Rabardel, L. "Non-classical Fe(II) spin-crossover behavior in polymeric iron(II) compounds of formula [Fe(NH2trz)3]X2 xH2O (NH2trz = 4-amino-1,2,4-triazloe; X = derivatives of naphthalene sulfonate." J. Mater. Chem. (1997) 7.10: 2069-2075.*

* cited by examiner

*Primary Examiner* — Alicia Chevalier
*Assistant Examiner* — Thomas Mangohig
(74) *Attorney, Agent, or Firm* — Sofer & Haroun, LLP

(57) ABSTRACT

A material is composed of at least one spin transition compound that corresponds to the formula $Fe_{1-m}M_m(R-Trz)_3 X_b Y_c$ (I) in which M is a metal having a $3d^4$, $3d^5$, $3d^6$ or $3d^7$ configuration, other than Fe; $0 \leq m \leq 1$; R-Trz represents a 1,2,4-triazole ligand carrying an R substituent on the nitrogen in the 4 position; R is an alkyl group or an $R^1R^2N$— group in which $R^1$ and $R^2$ represent, each independently of the other, H or an alkyl radical; X represents at least one noncoloring monovalent or divalent anion; Y represents at least one anion which has a coloring group; and b and c are chosen so that the electrical neutrality of the compound (I) is adhered to. A process for the preparation of this material and to its use as thermochromic pigment, as support for data storage or as optical limiter.

12 Claims, No Drawings ial. The present invention relates to a material essentially comprising a spin transition compound, to processes for the preparation of said material and to various applications of the material.

SPIN TRANSITION MATERIAL

RELATED APPLICATIONS

This application is a National Phase application of PCT/FR2008/000792, filed on Jun. 11, 2008, which in turn claims the benefit of priority from French Patent Application No. 07 04174, filed on Jun. 12, 2007, the entirety of which are incorporated herein by reference

BACKGROUND

1. Field of the Invention

The present invention relates to a material essentially comprising a spin transition compound, to processes for the preparation of said material and to various applications of the material.

2. Description of Related Art

It is known to use compounds which exhibit a spin, transition for various applications, in particular for information storage. Such compounds can in particular be coordination complexes comprising one or more metal centers having a $3d^4$, $3d^6$ or $3d^7$ configuration, one or more nitrogenous ligands and one or more anions, such as described, for example, in EP-0 543465, EP-0 666 561, EP-0 745 986 and EP-0 842 988.

EP-0 543 465 describes a process for the preparation of spin transition compounds and the use for information storage. The process consists in bringing together, on the one hand, the ligand and, on the other hand, an iron salt in an acid solution, in allowing to react, in order to obtain a precipitate, and in recovering the precipitate in the powder form. For the use for data storage, the complex obtained is reduced beforehand to a powder in order to be deposited on a support by various methods. The compounds mentioned correspond to one of the following formulae: $FeL_3(NO_3)_2$ in which L is a ligand of the 1,2,4-triazole or 4-amino-1,2,4-triazole type, in combination with the $NO_3^-$ anion; $Fe(ATP)_2.5Cl_2$, in which the ATP ligand is 4-amino-1,2,4-triazole in combination with Fe(II) and with $Cl^-$; $Fe(TP)_2Cl_2$ in which the TP ligand is 1,2,4-triazole, in combination with $Cl^-$; [Fe(2-aminomethylpyridine)$_3$]Cl$_2$EtOH, EtOH being ethanol; [Fe(1,10-phenanthroline)$_2$](NCS)$_2$; [Fe(1-propyltetrazole)$_6$](BF$_4$)$_2$; complexes of a metal M in combination with a mixture of several ligands (chosen from R-Trz, amines NL$_2$ and triazolates Trz-, M being Fe(II), Fe(III) or Co(II), R-Trz being a triazole carrying an R substituent, R and L being an alkyl or H) and with an anion chosen from $BF_4^-$, $ClO_4^-$, $CO_3^{2-}$, $Br^-$ and $Cl^-$, the complex additionally comprising a defined amount of water.

With the exception of [Fe(1,10-phenanthroline)$_2$(NCS)2], all these complexes are pink in color in the low spin (LS) state and white in the high spin (HS) state. The transition is brought about by heating or cooling and takes place between −20° C. and 100° C. These compounds exhibit a phenomenon of hysteresis which can range from a few degrees to a few tens of degrees.

EP-0 666 561 describes spin transition compounds which correspond to the formula Fe(II)(H-Trz)$_3$(X)$_2$ in which Trz is 1,2,4-triazole and (X)$_2$ represents the anion $(BF_4^-)_2$, $(ClO_4^-)_2$, $(Br^-)_2$, $(Cl^-)_2$ or $(CO_3^{2-})$. These compounds exhibit two crystalline phases, each having spin transitions associated with a change in color (white/pink) and for which the temperatures $T_{1/2\downarrow}$ and $T_{1/2\uparrow}$ are respectively less than and greater than ambient temperature. The preparation process is analogous to that described in EP-0 543 465 above.

EP-0 745 986 describes compounds corresponding to a formula analogous to that of the compounds of the "complex of a metal M in combination with a mixture of several ligands" type described in EP-0 543 465, M being here a metal ion of $d^5$, $d^6$ or $d^7$ configuration, the ligand being a dialkylaminotriazole and the anion comprising a sulfitoaryl, sulfitoalkyl, sulfitoaryl halide or sulfitoalkyl halide group. These specific compounds here a hysteresis amplitude of greater than 70° C. and a region of bistability centered exactly around ambient temperature. Said compounds are pink in the LS state and white in the HS state. The process for the preparation of the compounds, described very briefly, is analogous to that described in EP-0 543 465 above.

EP-0 842 988 describes spin transition chemical compounds and their use in display devices where a temperature threshold is exceeded. The compounds are formed by a network composed of molecules each formed by a metal-ligand complex and by an anion, and they comprise at least one water molecule bonded to the ligand via a hydrogen bond. The metal is chosen from those which have a $d^4$, $d^5$, $d^6$ or $d^7$ configuration. The ligand is 1,2,4-triazole carrying an R substituent comprising an OH group. The anions are nitrate and tosylate derivatives. The compounds corresponding to this definition have a temperature $T_{1/2\uparrow}$ of between 80 and 95° C. and a $T_{1/2\downarrow}$ of −170° C. They can be used in particular in devices intended to detect an accidentally high (of the order of 80° C.) storage temperature in storage buildings or transportation vehicles. The compounds are prepared by mixing a precursor of the metal center and a precursor of the ligand, at ambient temperature, and by removing the solvent by filtration after a precipitate has been obtained. The compound is obtained in the pulverulent form.

WO-06/002651 describes a material composed of nanoparticles of complexes of iron, of a triazole ligand and of at least one anion. This material, as a result of its nanometric nature, is of particular use especially as thermochromic pigment or for data storage.

Koningsbruggen Van P. et al. [Journal of Material Chemistry, The Royal Society of Chemistry, Cambridge, GB, vol. 7, No. 10, 2069-2075] describe compounds which correspond to the formula [Fe(NH$_2$trz)$_3$]X$_2$.xH$_2$ in which either the two X groups are noncoloring anions, such as $NO_3^-$, $ClO_4^-$, $Br^-$ and others, or the two X groups are anions which have coloring properties, in particular naphthalene anions carrying an $SO_3^-$ group. The color of these compounds changes from crimson-pink to white during heating to approximately 370K.

However, all these materials of the prior art specified have a very limited range of color variations since, depending on their spin state, they are either pink or crimson, on the one hand, or white, on the other hand.

A few compounds are known for which a rise in temperature brings about a change in color other than "pink-white". For example, Arslan et al. [Dyes and Pigments, Elsevier Applied Science Publishers, Barking, GB, vol. 75, No. 3, 521-525] describe a complex [Zn(Hsal)$_2$(H$_2$O)(abpy)].H$_2$O which changes from brown to crimson during heating. "abpy" represents azobis-pyridine. In these compounds, the change in color is not due to a spin transition but to a phase transition, which is a relatively slow phenomenon, whereas spin transition is a rapid and virtually inexhaustible phenomenon in the solid phase.

Kume Shoko et al. [Chemical Communications, No. 23, 2006, 2442-2444] describe an $Fe^{II}$ triazole complex [Fe(1)$_3$(BF$_4$)$_2$] corresponding to the formula

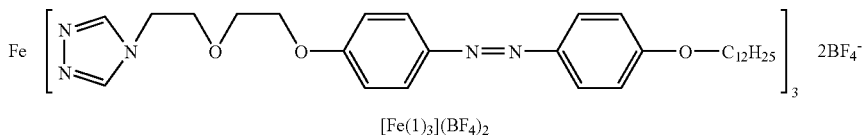

[Fe(1)₃](BF₄)₂ which changes from yellow to orange. This compound certainly makes possible a change in color other than "pink-white". However, the change in color originates not from a spin transition but from a photo-isomerization of the ligand at a given temperature which modifies the absorption of the compound. The change in color occurs without hysteresis and cannot be adjusted.

OBJECTS AND SUMMARY

The aim of the present invention is to provide materials which rapidly change in color under the effect of a variation in temperature, with or without hysteresis, the change in color being other than pink or white and being able to be adjusted. This property is obtained by the use of an iron complex in which the ligand is combined with at least one anion which has coloring properties and at least one anion which does not have coloring properties.

A subject matter of the present invention is consequently a novel material, processes for obtaining said material and applications of said material. The material according to the present invention is composed of at least one compound corresponding to the formula $$Fe_{1-m}M_m(R\text{-}Trz)_3X_bY_c \qquad (I)$$

in which:

M is a metal, other than Fe, having a $3d^4$, $3d^5$, $3d^6$ or $3d^7$ configuration;

$0 \leq m < 1$, preferably $m \leq 0.8$;

R-Trz represents a 1,2,4-triazole ligand carrying an R substituent on the nitrogen in the 4 position;

R is an alkyl group or an $R^1R^2N$-group in which $R^1$ and $R^2$ represent, each independently of the other, H or an alkyl radical;

X represents at least one noncoloring monovalent or divalent anion;

Y represents at least one anion which has a coloring group;

$b>0$ and $c>0$, b and c being chosen so that the electrical neutrality of the compound (I) is adhered to.

Preferably, b and c are such that $10^{-5} \leq c/b \leq 0.1$ (in moles).

A compound which corresponds to the above definition is capable of reversibly changing in spin state during heating and during cooling, with a change in color associated with each change in spin.

DETAILED DESCRIPTION

The material according to the invention can be composed of:

just one compound (I) in which Y represents a coloring anion or several different coloring anions, for example two coloring anions $Y^1$ and $Y^2$;

several different compounds which each correspond to the formula (I); or a compound corresponding to the formula (I) and a compound $Fe_{1-m}M_m(R\text{-}Trz)_3X_b$, that is to say a compound without a coloring anion.

X can represent one or more noncoloring anions, preferably one or two anions $X^1$ and $X^2$. A monovalent anion X can be chosen from $BF_4^-$, $PF_6^-$, $ClO_4^-$, $Br^-$, $Cl^-$, $NO_3^-$, $CF_3SO_3^-$ and $CH_3SO_3^-$. A divalent anion X is preferably chosen from $SO_4^{2-}$ and $CO_3^{2-}$. Mention may be made, as examples of combination of anions, of the $BF_4^-$ and $NO_3^-$ pair, the $Br^-$ and $NO_3^-$ pair or the $Cl^-$ and $NO_3^-$ pair.

The choice of the ligands R-Trz and of the anions X makes it possible to control the spin transition (in particular the sudden nature, the presence of hysteresis and the position of the transition.

An anion Y is preferably chosen from coloring anions which have at least two aromatic rings and at least one $SO_3^-$ group. Such anions are provided in particular by "acid dye" or "direct dye" or "brilliant dye" or "mordant dye" compounds.

The anion of these dyes can comprise:

an azo group, such as, for example, C.I. Acid Orange 5, which is the monosodium salt of 4-[[4-(phenylamino)phenyl]azo]benzenesulfonic acid, or Acid Yellow 23, which is tartrazine, corresponding to the formula:

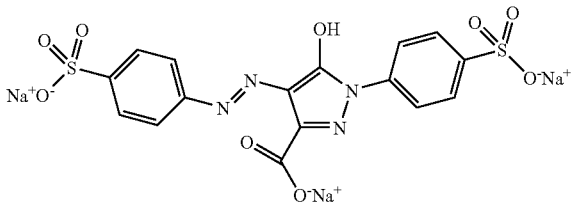

or Methyl Orange or Acid Orange 52 (helianthine), corresponding to the formula:

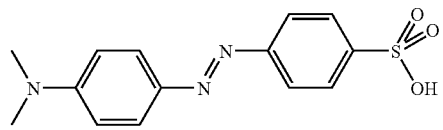 [SMILES: CN(C)c1ccc(/N=N/c2ccc(S(=O)(=O)O)cc2)cc1]

or various Direct Scarlet products; or C.I. Direct Blue 1, corresponding to the formula:

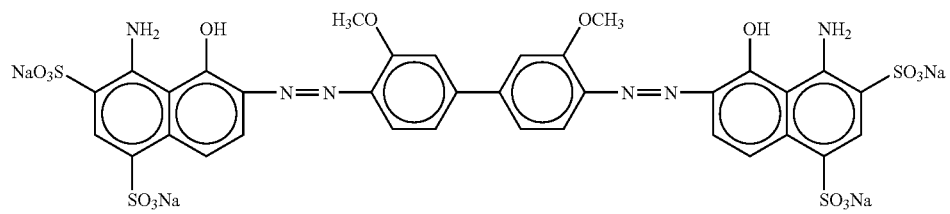

or C.I. Acid Red 27, corresponding to the formula:

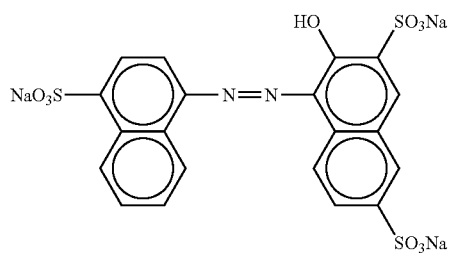

a group derived from anthraquinone, for example C.I. Reactive Blue 4, corresponding to the formula:

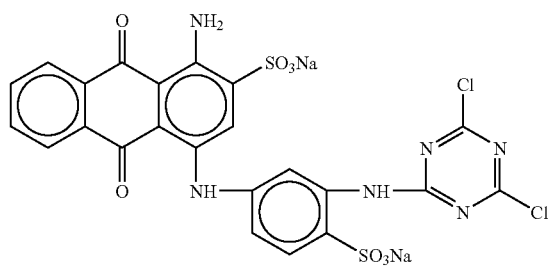

a group derived from a quinoline (C.I. Acid Yellow 3; D&C. Yellow No. 30).

Mention may be made, by way of examples, among dyes referred to as acid dyes, of the following products: Acid Black ATT-M, Acid Black 10B (Acid Black 1), Acid Black BG (Acid Black 31), Acid Black BRN, Acid Blue Black BR (Acid Black 24), Acid Bright Yellow G (Acid Yellow 11), Acid Bright Yellow 2G (Acid Yellow 17), Acid Brown 2R (Acid Brown 14), Acid Brown RL (Acid Brown 2), Acid Corith N-5BL (Acid Red 299), Acid Chrome Grey BS (Mordant Black 13), Acid Dark Blue 5R (Acid Blue 113), Acid Dark Blue GR (Acid Blue 120), Acid Green GS (Acid Green 25), Acid Light Red 2G (Acid Red 1), Acid Milling Yellow G (Acid Yellow 117), Acid Navy Blue (Acid Blue 92), Acid Orange GS (Acid Orange 33), Acid Orange II (Acid Orange 7), Acid Red A (Acid Red 88), Acid Red B (Acid Red 14), Acid Red G (Acid Red 35 or 1), Acid Red 6B (Acid Violet 35), Acid Scarlet GR (Acid Red 73), Acid Scarlet MOO (Acid Red 73), Acid Scarlet 3R (Acid Red 18), Acid Blue 1 (Patent Blue VF or Sulfan Blue), Acid Dark, Acid Fuschin, Acid Green, Acid Orange 52 (Methyl Orange or helianthine), Acid Violet or Acid Yellow 23 (tartrazine).

Mention may be made, by way of examples, among dyes referred to as direct dyes, of the following products: Direct Black TBRN, Direct Black 38, Direct Bordeaux (Direct Red 23), Direct Chrysophenine G (Direct Yellow 12), Direct Copper Blue 2R or 2B (Direct Blue 86), Direct Dark Brown M (Direct Brown 2), Direct Fast Black G (Direct Black 19), Direct Fast Black GF (Direct Black 22), Direct Fast Blue 5B (Direct Blue 86), Direct Fast Green BLL (Direct Green 26), Direct Green B (Direct Green 26), Direct Grey D (Direct Black 17), Direct Pink 12B (Direct Red 31), Direct Scarlet 4BS (Direct Red 23), Direct Sky Blue 5B (Direct Blue 15), Direct Turquoise Blue (Direct Blue 86), Direct Violet or Trypan Blue (Direct Blue 14).

The proportions of anions X and Y are such that the electrical neutrality of the compound is adhered to.

The color of each spin state of the material according to the invention can be adjusted by appropriately choosing the anion or anions X and Y and by controlling their respective proportions in the material.

It is necessary for the proportion of coloring anion Y to be greater than a certain threshold in order to prevent a compound being obtained which exhibits a pink color in the low spin state and a white color in the high spin state. It is also necessary for the proportion of coloring anion to be less than a certain threshold beyond which the colors corresponding to the low spin state and to the high spin state are difficult to distinguish. The limits depend in particular on the degree of coloring nature of the anion Y. Thus, the lower concentration limit and the upper concentration limit of an anion Y with a high coloring power are lower than those of an anion with a low coloring power.

Generally, a material according to the invention preferably comprises anions in a proportion such that the c/b molar ratio (that is to say, "number of moles of Y"/"number of moles of X") is less than or equal to 0.1 and greater than or equal to $10^{-5}$.

A person skilled in the art, who knows the colors associated with the various dyes from which the anions Y result, will know how to determine, by routine tests, the lower and upper limits between which the proportion of coloring anion Y has to be maintained in order to obtain the necessary contrasts between the colors of the material in its low spin state and in its high spin state, according to the application envisaged.

When an R substituent is an alkyl group, it is preferably chosen from alkyl groups having from 1 to 8 carbon atoms, more particularly from 1 to 4 carbon atoms. When an R substituent is an $R^1R^2N$-group, $R^1$ and $R^2$ represent, independently of one another, preferably H or an alkyl group having from 1 to 8 carbon atoms, more particularly from 1 to 4 carbon atoms.

In a specific embodiment, m=0 and the material according to the invention corresponds to the formula $Fe(R-Trz)_3(X)_b(Y)_c$.

In another embodiment, m≠0. M then acts as doping agent for the spin transition phenomenon of the compound $Fe_{1-m}M_m(R-Trz)_3(X)_b(Y)_c$. An increase in m lessens the sudden nature of the transition and the intensity of the color corresponding to the low spin state. Mention may be made, as examples of metal M, of the zinc(II), manganese(II), nickel (II) and cobalt(II) ions. The presence of an element M as partial replacement of Fe makes it possible to lessen the sudden nature of the spin transition, according to the use of the material.

The material according to the invention can be in the powder form. The particles forming the powder can have a nanometric or macroscopic size. Nanometric particles is understood to mean particles having a mean diameter of less than 500 nm. Macroscopic particles is understood to mean particles having a mean diameter of greater than 500 nm and less than 500 μm, more particularly between 600 nm and 100 μm.

When the material is provided in the form of nanometric particles, said nanometric particles can be coated with a film of silica. The presence of silica at the surface of the particles makes it possible to modify their surface tension and to graft functional groups of use according to the applications of the spin transition material.

The material proposed is obtained by bringing a solution comprising at least one Fe(II) salt of an anion X, optionally a salt of the metal M and of an anion X identical to or different from the anion X of the iron salt, and a precursor of the coloring anion(s), into contact with a solution of ligand R-Trz and by then precipitating, by cooling, the product obtained.

The contacting operation can advantageously be carried out at ambient temperature.

The amounts of the various reactants introduced into the reaction medium are preferably those which correspond to the stoichiometry of the formula $Fe_{1-m}M_m(R\text{-}Trz)_3X_bY_c$ of the desired material, that is to say to the values respectively chosen for m, b and c.

The material obtained can be used either in the form of a suspension in the aqueous medium in which it is obtained or in the form of a dry powder.

A material according to the present invention can be obtained in the form of nanoparticles by reverse micelle synthesis or by a microemulsion synthesis.

The process by reverse micelle synthesis comprises the following stages, when $m \neq 0$, that is to say in the absence of metal M:

a) preparation of an emulsion of the water-in-oil type by addition, with vigorous stirring, of a composition of oil possessing surfactant properties type to an aqueous solution comprising at least one iron salt of the anion X, ascorbic acid and a precursor of the anion Y;

b) preparation of an emulsion of the water-in-oil type by addition, with vigorous stirring, of a composition of oil possessing surfactant properties type to an aqueous solution of the ligand R-Trz;

c) mixing the two emulsions with vigorous stirring;

d) precipitation of the nanoparticles by addition of a solvent which does not modify the structure of the nanoparticles and which denatures the emulsion, for example ethyl ether.

Stirring for 1 to 10 min is generally sufficient to suitably mix the two emulsions.

The solvent used to denature the emulsion and to bring about the precipitation of the spin transition material is chosen according to the surface-active agent used. This choice is within the scope of a person skilled in the art. The precipitate obtained can be extracted from the aqueous medium by several "washing/centrifuging" cycles, followed by evaporation of the washing solvent. The washing solvent is advantageously the solvent which was used to precipitate the nanoparticles.

For the preparation of a material comprising two types of anions Y, namely $Y^1$ and $Y^2$, the aqueous solution of stage a) comprises both a precursor of the anion $Y^1$ and a precursor of the anion $Y^2$.

For the preparation of a material comprising two types of anions X, namely $X^1$ and $X^2$, the aqueous solution of stage a) comprises both an iron salt of $X^1$ and an iron salt of $X^2$.

The composition of the oil possessing surfactant properties type can be either a composition obtained by addition of a surfactant to an oil or a single product having both surfactant properties and oil properties (such as the product sold under the names Lauropal®, Tergitol®, or Ifralan®).

The size of the particles formed can be controlled in particular by the choice of the reaction temperature and/or of the duration of contacting of the two microemulsions prepared respectively during stages a) and b). All things otherwise being equal, an increase in the duration and/or in the temperature promotes an increase in the size of the final particles. The process by a microemulsion synthesis comprises the following stages, when m=0, that is to say in the absence of metal M:

a. preparation of a microemulsion of the water-in-oil type by addition of an aqueous solution comprising at least one iron salt of the anion X and of a precursor of the coloring anion Y to a solution of a surfactant in an oil (n-heptane, for example) and dispersing until a clear solution is obtained;

b. preparation of a microemulsion of the water-in-oil type by addition of an aqueous solution of ligand (R-Trz) to a solution of a surfactant in an oil and dispersing until a clear solution is obtained;

c. mixing the two microemulsions and treating the mixture with ultrasound until a clear solution is obtained;

d. precipitation of the nanoparticles by addition of a solvent which does not modify the structure of the nanoparticles but which denatures the emulsion, for example ethanol.

Dispersing is advantageously carried out by treatment with ultrasound.

In this embodiment too, the precipitate obtained can be extracted from an aqueous medium by several "washing/centrifuging" cycles, followed by evaporation of the washing solvent.

For the preparation of a material comprising several different anions Y, the aqueous solution of stage a) comprises a precursor of each of the anions Y which can be chosen from the abovementioned dyes.

For the preparation of a material comprising several different anions X, the aqueous solution of stage a) comprises an iron salt of each of the anions X.

The proportions of solvent, of surfactant and of oil which are required in order to obtain a microemulsion are determined from the phase diagram of the ternary mixture. The ternary phase diagram is available in the literature for numerous solvent/oil/surfactant combinations. The determination of a specific ternary diagram is within the scope of a person skilled in the art.

In both methods of preparation of the materials of the invention in the form of nanoparticles, when $m \neq 0$, that is to say in the presence of metal M:

when just one anion X is desired in the material, an aqueous solution of M salt is prepared and is added to the aqueous solution of Fe salt of X, before bringing into contact with the "surfactant+oil" mixture;

when several different noncoloring anions X are desired in the material, a solution comprising at least one iron salt of one of the anions X and at least one M salt of an anion $X^1$ other than X is prepared.

For the preparation of a material according to the invention in the form of spin transition compound nano-particles coated with silica, in the two above methods of preparation, a silyl derivative is added to the reaction medium, before denaturation of the micelle or of the microemulsion (that is to say, before stage d) in the two embodiments described above). Mention may be made, as examples of silyl derivative, of tetraethoxy-silane, n-octadecyltriethoxysilane and (n-octyl) tri-ethoxysilane.

The material according to the present invention can be in the form of macroscopic particles. This form of the material can be obtained by a process consisting in adding an aqueous solution of iron salt of X and optionally of metal M salt of X, comprising a controlled amount of a precursor of the coloring anion Y, to an aqueous solution of ligand R-Trz and in extracting the precipitate formed. This embodiment makes it possible to prepare the material in the form of macroscopic particles, the color obtained being given directly by the coloring anion or anions Y introduced into the reaction medium.

For the preparation of a material comprising several different anions Y, the aqueous solution of stage a) comprises a precursor of each of the anions Y. These precursors are chosen from the abovementioned dyes.

For the preparation of a material comprising several different anions X, the aqueous solution of stage a) comprises an iron salt of each of the anions X.

A few specific embodiments of the preparation of the materials corresponding to the definition of the invention, in the form of macroscopic particles, which makes it possible to obtain highly varied ranges of color are described below.

A material according to the invention can be composed of two compounds (I) having the same ligand and different anions Y. In a specific embodiment, a material according to the invention is prepared in several stages:

preparation of a compound $Fe_{1-m}M_m(R\text{-}Trz)_3X_bY^1_{c1}$ and of a compound $Fe_{1-m}M_m(R\text{-}Trz)_3X_{b'}Y^2_{c2}$ by one of the processes described above, X representing, in each of these compounds, one or more anions and $Y^1$ and $Y^2$ being different and each representing just one anion, it being understood that the indices b, b', c1 and c2 are chosen in order for the electrical neutrality of the compounds to be adhered to;

for each of the compounds, extraction by washing/centrifuging cycles;

mixing the two compounds obtained in the solid state.

Thus, it is possible, for example, to prepare a first material exhibiting a blue color in the high spin state and a second material exhibiting a yellow color in the high spin state and to mix the two powders obtained, so as to obtain a material exhibiting a green color in the high spin state.

A material according to the invention can be composed of a compound $Fe_{1-m}M_m(R\text{-}Trz)_3X_bY_c$ (I) and of a compound $Fe_{1-m}M_m(R'\text{-}Trz)_3X'_{b'}$ (without a coloring anion). In this specific embodiment, a material according to the invention is prepared in several stages:

preparation of a compound $Fe_{1-m}M_m(R\text{-}Trz)_3X_bY_c$ in which Y represents one or more coloring anions by one of the processes described above;

preparation of a compound $Fe_{1-m}M_m(R'\text{-}Trz)_3X'_{b'}$ (R and R' being identical or different and X and X' being identical or different) by a process as defined above but omitting the precursor of the coloring anion Y;

for each of the compounds, extraction by washing/centrifuging cycles;

mixing the two compounds obtained in the solid state.

A compound of the $Fe_{1-m}M_m(R'\text{-}Trz)_3X'_{b'}$ type is known to exhibit a pink color in the low spin state and a white color in the high spin state. Mixing it with a colored compound $Fe_{1-m}M_m(R\text{-}Trz)_3X_bY_c$ according to the invention makes it possible to modify the initial color of the compound $Fe_{1-m}M_m(R\text{-}Trz)_3X_bY_c$ and to thus obtain varied ranges of color.

A material according to the invention can be composed of a mixture of compounds (I) which differ in the ligand, in X and in Y. In this specific embodiment, a material according to the invention is prepared in several stages:

preparation of a compound $Fe_{1-m}M_m(R\text{-}Trz)_3X_bY_c$ in which Y represents one or more coloring anions by one of the processes defined above;

preparation of a compound $Fe_{1-m}M_m(R'\text{-}Trz)_3X'_{b'}Y'_{b'}$ (R and R' being different, X and X' being different and Y and Y' being different) by a process as described above;

for each of the compounds, extraction by washing/centrifuging cycles;

mixing the two compounds obtained in the solid state.

A material according to the present invention in the solid state exhibits three switching colors when it comprises two different groups Y and two different groups $Fe_{1-m}M_m(R\text{-}Trz)$. This result can be obtained by:

a compound $Fe_{1-m}M_m(R\text{-}Trz)_3X_bY_c$ in which X represents two different noncoloring anions and Y represents two different coloring anions; or a mixture of two compounds $Fe_{1-m}M'_{m'}(R'\text{-}Trz)_3X'_bY'_c$ and $Fe_{1-m}M_m(R\text{-}Trz)_3X_bY_c$ in which Y and Y' are different and at least one of the pairs M-M', X-X' or R-R' is composed of two different components.

The material composed of the mixture of the two compounds in the powder form is a thermochromic material which exhibits three switching colors. This type of material is advantageous in particular in the field of indicators where the temperature threshold has been exceeded. Each of the groups $Fe_{1-m}M_m(R\text{-}Trz)_3X$ and $Fe_{1-m}M'_m(R'\text{-}Trz)_3X'$ possesses a transition with characteristics which are specific to it (as regards the position, the sudden nature and the presence of hysteresis). The choice of the amounts of each of the compounds in the material makes it possible to adjust the amplitude of the transition and of the intermediate color.

The material of the present invention is of particular use as thermochromic pigment in the field of paints and varnishes, plastics technology, signage, decoration and data securing. By way of example, in the field of plastics technology, the application of a varnish is often carried out in the form of a layer with a thickness of a few microns. The particles proposed can be incorporated directly into a polymer matrix which will be applied to a substrate in the form of a layer with a thickness of the order of a micrometer or a nanometer.

The material in the form of nanoparticles according to the invention is in addition of use for data storage. The nanoparticles constitute a genuine "molecular memory" using the phenomenon of spin transition. A bit of information can thus be stored in each nanoparticle. The perfect transparency of a disc composed of a polymer matrix doped with these bistable nanoparticles makes it possible to envisage applications in the field of bulk data storage (holography). The present invention exhibits the advantage of offering a range of particles with adjustable switching wavelengths.

The significant modification in color (that is to say, of the absorption spectrum) associated with the phenomenon of spin transition is reflected by a change in the refractive index of the material between the low spin state and the high spin state. The respective refractive indices of the two states can be adjusted in order to render the medium transparent when the molecules are in the HS state. At high optical energy, the photoinduced effects can bring about switching from the HS state to the LS state and can thus bring about a variation in the refractive index. The initially transparent medium then becomes opaque. This phenomenon makes it possible for the nanoparticles to be used in the field of optical limiters.

It should be noted that, under the effect of an external pressure, the low spin state, which is smaller in volume, is favored. For this reason, the insertion of nanoparticles of a material according to the invention into a piezoelectric (polymer) matrix makes it possible to control a modification in color which can be used in the field of optical filters and "intelligent" glazing.

The present invention is described in more detail with the help of the following examples, which are given by way of illustration and to which the invention is, of course, not limited.

EXAMPLE 1

Preparation of Macroscopic Particles in which Y=Patent Blue VF Acid Blue 1

5 ml of an aqueous solution comprising 590 mg of 4-amino-1,2,4-triazole and 5 ml of an aqueous solution comprising 500 mg of $FeBr_2$ and 1 ml of a solution of Patent Blue VF dye, the formula of which is given below:

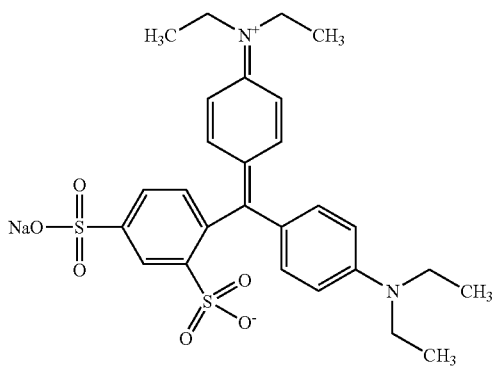

are mixed at ambient temperature.

After mixing for 1 hour, the reaction medium is cooled and the precipitate which has formed is washed with water.

Various samples were prepared according to the above procedure, using dye solutions having different concentrations of Patent Blue VF dye.

The colors of the low spin and high spin states obtained as a function of the concentration C (in mol/l) of the dye solution used are presented in table 1. The color is indicated in particular by the spectral trichromatic components of the CIE XYZ 1931 system and of the L*a*b* CIE 1976 chromatic space. The change in the low spin color and the high spin color, when the proportion of coloring anion increases in the material, is shown in this table.

TABLE 1

| C (mol/l) | Color, low spin state | Color, high spin state |
|---|---|---|
| $4.14 \times 10^{-7}$ | PINK<br>x = 0.336; y = 0.319;<br>z = 0.346<br>L = 89.32; a = 7.70;<br>b = −4.91 | WHITE<br>x = 0.333; y = 0.334;<br>z = 0.3325<br>L = 97.96; a = −0.20;<br>b = 0.31 |
| $8.28 \times 10^{-7}$ | PINK<br>x = 0.333; y = 0.321;<br>z = 0.346<br>L = 90.39; a = 5.69;<br>b = −4.52 | PALE BLUE<br>x = 0.329; y = 0.332;<br>z = 0.339<br>L = 97.00; a = −1.35;<br>b = −1.29 |
| $6.63 \times 10^{-6}$ | x = 0.318; y = 0.316;<br>z = 0.366<br>L = 86.01; a = 1.00;<br>b = −8.93 | x = 0.308; y = 0.326;<br>z = 0.367<br>L = 91.50; a = −8.68;<br>b = −7.49 |
| $2.65 \times 10^{-5}$ | x = 0.329; y = 0.322;<br>z = 0.349<br>L = 89.79; a = 3.36;<br>b = −5.10 | x = 0.322; y = 0.333;<br>z = 0.345<br>L = 95.19; a = −5.10;<br>b = −2.24 |
| $5.30 \times 10^{-5}$ | x = 0.329; y = 0.322;<br>z = 0.349<br>L = 89.79; a = 3.36;<br>b = −5.10 | x = 0.322; y = 0.333;<br>z = 0.345<br>L = 95.19; a = −5.10;<br>b = −2.24 |
| $2.12 \times 10^{-4}$ | DARK BLUE<br>x = 0.298; y = 0.315;<br>z = 0.387<br>L = 82.02; a = −7.92;<br>b = −11.85 | CYAN BLUE<br>x = 0.288; y = 0.325;<br>z = 0.387<br>L = 85.82; a = −17.10;<br>b = −10.47 |

EXAMPLE 2

Preparation of Macroscopic Particles in which Y=Tartrazine Acid Yellow 23

The same procedure was followed as that described in example 1, Patent Blue being replaced with tartrazine.

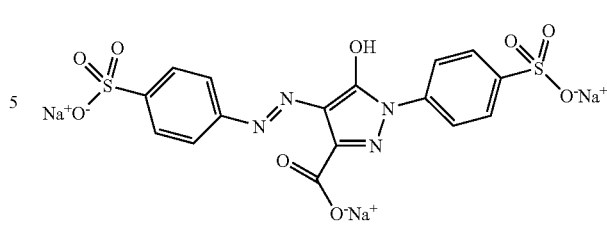

The colors of the low spin and high spin states obtained as a function of the concentration of the dye solution used are presented in table 2. The color is indicated by the spectra: trichromatic components of the CIE XYZ 1931 system and of the L*a*b* CIE 1976 chromatic space. The change in the low spin color and the high spin color, when the proportion of coloring anion increases in the material, is shown in this table.

TABLE 2

| C (mol/l) | Color, low spin state | Color, high spin state |
|---|---|---|
| $2.19 \times 10^{-7}$ | PINK<br>x = 0.336; y = 0.319;<br>z = 0.346<br>L = 89.32; a = 7.70;<br>b = −4.91 | WHITE<br>x = 0.333; y = 0.334;<br>z = 0.3325<br>L = 97.96; a = −0.20;<br>b = 0.31 |
| $4.39 \times 10^{-7}$ | PINK<br>x = 0.338; y = 0.324;<br>z = 0.338<br>L = 89.08; a = 6.63;<br>b = −2.55 | PALE YELLOW<br>x = 0.341; y = 0.341;<br>z = 0.317<br>L = 96.82; a = −0.12;<br>b = 4.66 |
| $1.76 \times 10^{-6}$ | x = 0.342; y = 0.325;<br>z = 0.333<br>L = 87.83; a = 7.87;<br>b = −1.44 | x = 0.347; y = 0.346;<br>z = 0.306<br>L = 96.31; a = 0.34;<br>b = 7.77 |
| $1.40 \times 10^{-5}$ | x = 0.346; y = 0.327;<br>z = 0.328<br>L = 85.97; a = 8.43;<br>b = −0.20 | x = 0.353; y = 0.352;<br>z = 0.295<br>L = 95.35; a = 0.41;<br>b = 11.07 |
| $1.12 \times 10^{-4}$ | ORANGE<br>x = 0.361; y = 0.352;<br>z = 0.288<br>L = 90.19; a = 3.99;<br>b = 11.89 | DARK YELLOW<br>x = 0.371; y = 0.368;<br>z = 0.262<br>L = 93.92; a = 1.36;<br>b = 20.26 |

EXAMPLE 3

Preparation of Macroscopic Particles in which $Y^1$=Patent Blue and $Y^2$=Tartrazine The same procedure was followed as that described in example 1, a mixture of Patent Blue and tartrazine being used as dye.

The colors of the low spin and high spin states obtained as a function of the concentration of dye used are presented in table 3. The color is indicated by the spectral trichromatic components of the CIE XYZ 1931 system and of the L*a*b* CIE 1976 chromatic space. In the column of the concentrations, a represents the concentration of tartrazine (mol/l) and b represents the concentration of Patent Blue (mol/l) of the dye solution. The change in the low spin color and high spin color, when the proportion of coloring anion increases in the material, is shown in this table.

TABLE 3

| C (mol/l) | Color, low spin state | Color, high spin state |
|---|---|---|
| $a = 1.75 \times 10^{-7}$ | PINK | WHITE |
| $b = 1.65 \times 10^{-7}$ | x = 0.336; y = 0.319; | x = 0.333; y = 0.334; |
| | z = 0.346 | z = 0.3325 |
| | L = 89.32; a = 7.70; | L = 97.96; a = −0.20; |
| | b = −4.91 | b = 0.31 |
| $a = 7.02 \times 10^{-6}$ | PINK | PALE GREEN |
| $b = 6.62 \times 10^{-7}$ | x = 0.341; y = 0.329; | x = 0.342; y = 0.349; |
| | z = 0.331 | z = 0.309 |
| | L = 87.00; a = 5.20; | L = 93.99; a = −3.29; |
| | b = −0.34 | b = 7.69 |
| $a = 2.81 \times 10^{-6}$ | GREEN-GREY | GREEN |
| $b = 2.65 \times 10^{-6}$ | x = 0.336; y = 0.327; | x = 0.336; y = 0.343; |
| | z = 0.336 | z = 0.320 |
| | L = 90.21; a = 4.17; | L = 95.89; a = −3.25; |
| | b = −1.67 | b = 4.48 |
| $a = 1.12 \times 10^{-5}$ | DARK GREEN | GREEN |
| $b = 1.06 \times 10^{-5}$ | x = 0.332; y = 0.375; | x = 0.332; y = 0.388; |
| | z = 0.293 | z = 0.280 |
| | L = 72.13; a = −15.36; | L = 71.74; a = −19.06; |
| | b = 12.03 | b = 15.64 |

The examples described above confirm that the spin transition materials of the iron complex type, the anions of which are not coloring, are all pink in the low spin state and white in the high spin state. These colors are modified when the noncoloring anions are partially replaced by coloring anions, when the content of coloring anion exceeds a certain threshold. When the proportion of coloring anion is high, the dominant color is the intrinsic color of the dye from which the anion originates. The intermediate proportions make it possible to vary the color in the low spin state and the color in the high spin state.

The materials of the invention thus provide spin transition compounds which vary between highly varied colors which can be adjusted by modifying the relative proportions of coloring anion and of noncoloring anion. The temperature of the transition, the more or less sudden nature and the hysteresis are governed by the combination formed by the ligand and the noncoloring anion. The present invention thus offers a wide choice of spin transition materials in terms of transition temperature, of colors and of particle size.

What is claimed is:

1. A spin transition material composed of at least one compound corresponding to the formula $$Fe_{1-m}M_m(R\text{-}Trz)_3X_bY_c \quad (I)$$

in which:
M is a metal, other than Fe, having a $3d^4$, $3d^5$, $3d^6$ or $3d^7$ configuration;
$0 \leq m < 1$;
R-Trz represents a 1,2,4-triazole ligand carrying an R substituent on the nitrogen in the 4 position;
R is an alkyl group or an $R^1R^2N$— group in which $R^1$ and $R^2$ represent, each independently of the other, H or an alkyl radical;
X represents at least one noncoloring monovalent or divalent anion selected from the group consisting of $BF_4^-$, $PF_6^-$, $ClO_4^-$, $Br^-$, $Cl^-$, $NO_3^-$, $CF_3SO_3^-$, $CH_3SO_3^-$, $SO_4^{2-}$ and $CO_3^{2-}$;
Y represents at least one coloring anion which has at least two aromatic rings and at least one $SO_3^-$ group;
b>0 and c>0, b and c being chosen so that the electrical neutrality of the compound (I) is adhered to and b and c are such that $10^{-5} \leq c/b \leq 0.1$ (in moles), so as to provide a spin transition associated with a change in color being other than pink or white.

2. The spin transition material as claimed in claim 1, wherein the material is composed of:
just one compound (I) in which Y represents a coloring anion or several different coloring anions;
several different compounds which each correspond to the formula (I); or
a compound corresponding to the formula (I) and a compound $Fe_{1-m}M_m(R\text{-}Trz)_3X_b$, without a coloring anion.

3. The spin transition material as claimed in claim 1, wherein R is an alkyl group having from 1 to 8 carbon atoms or an $R^1R^2N$— group in which $R^1$ and $R^2$ represent, independently of one another, H or an alkyl group having from 1 to 8 carbon atoms.

4. The spin transition material as claimed in claim 1, wherein the compound (I) corresponds to the formula $Fe(R\text{-}Trz)_3(X)_b(Y)_c$.

5. The spin transition material as claimed in claim 1, wherein the compound (I) corresponds to the formula $Fe_{1-m}M_m(R\text{-}Trz)_3(X)_b(Y)_c$ in which m>0 and M is chosen from zinc(II), manganese(II), nickel(II) and cobalt(II).

6. The spin transition material as claimed in claim 1, wherein said material is composed as a thermochromic pigment, for either one of support for data storage or an optical limiter.

7. The spin transition material as claimed in claim 1, wherein the material is in the form of macroscopic particles having a mean diameter of greater than 500 nm and of less than 500 μm.

8. The material as claimed in claim 1, wherein the material is in the form of a suspension in an aqueous medium.

9. The spin transition material as claimed in claim 1, wherein the material is in the form of nanometric particles having a size less than 500 nm.

10. The material as claimed in claim 9, wherein the nanometric particles are coated with a film of silica.

11. The spin transition material as claimed in claim 1, wherein the material is in the form of a powder.

12. The spin transition material as claimed in claim 11, exhibiting three switching colors, wherein the material is composed of:
a compound $Fe_{1-m}M_m(R\text{-}Trz)_3X_bY_c$ in which X represents two different noncoloring anions and Y represents two different coloring anions; or
a mixture of two compounds $Fe_{1-m}M'_m(R\text{-}Trz)_3X'_bY'_c$ and $Fe_{1-m}M_m(R\text{-}Trz)_3X_bY_c$ in which Y and Y' are different and at least one of the pairs M-M', X-X' or R-R' is composed of two different components.

* * * * *

UNITED STATES PATENT AND TRADEMARK OFFICE
CERTIFICATE OF CORRECTION

PATENT NO.        : 8,709,599 B2
APPLICATION NO.   : 12/664008
DATED             : April 29, 2014
INVENTOR(S)       : Letard et al.

It is certified that error appears in the above-identified patent and that said Letters Patent is hereby corrected as shown below:

In the Claims

Column 14, Claim 12, Line 53: Between the words "compounds" and "and" is the formula:
"Fe.sub1 -m'M'.subm'(R-Trz)sub3X'.subbY'.subc"

It should read as follows: "Fe.sub1 -m'M'.subm'(R'-Trz)sub3X'.subbY'.subc" the R should be R'

Signed and Sealed this
Twenty-ninth Day of July, 2014

Michelle K. Lee
*Deputy Director of the United States Patent and Trademark Office*